US00PP21203P2

(12) United States Plant Patent
Mitchell et al.

(10) Patent No.: US PP21,203 P2
(45) Date of Patent: Aug. 17, 2010

(54) ***CLEMATIS* PLANT NAMED 'ROBLOM'**

(50) Latin Name: *Clematis hybrida*
Varietal Denomination: RobloM

(76) Inventors: Robinson Charles Mitchell, 28 Vardon Crescent, Christchurch 8061 (NZ); Lorna Mitchell, 28 Vardon Crescent, Christchurch 8061 (NZ)

( * ) Notice: Subject to any disclaimer, the term of this patent is extended or adjusted under 35 U.S.C. 154(b) by 0 days.

(21) Appl. No.: 12/319,514

(22) Filed: Jan. 8, 2009

(51) Int. Cl.
*A01H 5/00* (2006.01)

(52) U.S. Cl. ..... Plt./228

(58) Field of Classification Search ..... Plt./228
See application file for complete search history.

*Primary Examiner*—June Hwu

(57) ABSTRACT

A new and distinct *Clematis* cultivar named 'RobloM' is disclosed, characterized by having distinctive flower coloration, with an unusual white bar on a background of purple/pink. Additionally, the new variety characteristically blooms very early and has a very rapid growth habit. The new variety is a *Clematis*, normally produced as an outdoor garden or container plant.

1 Drawing Sheet

Figure 1:
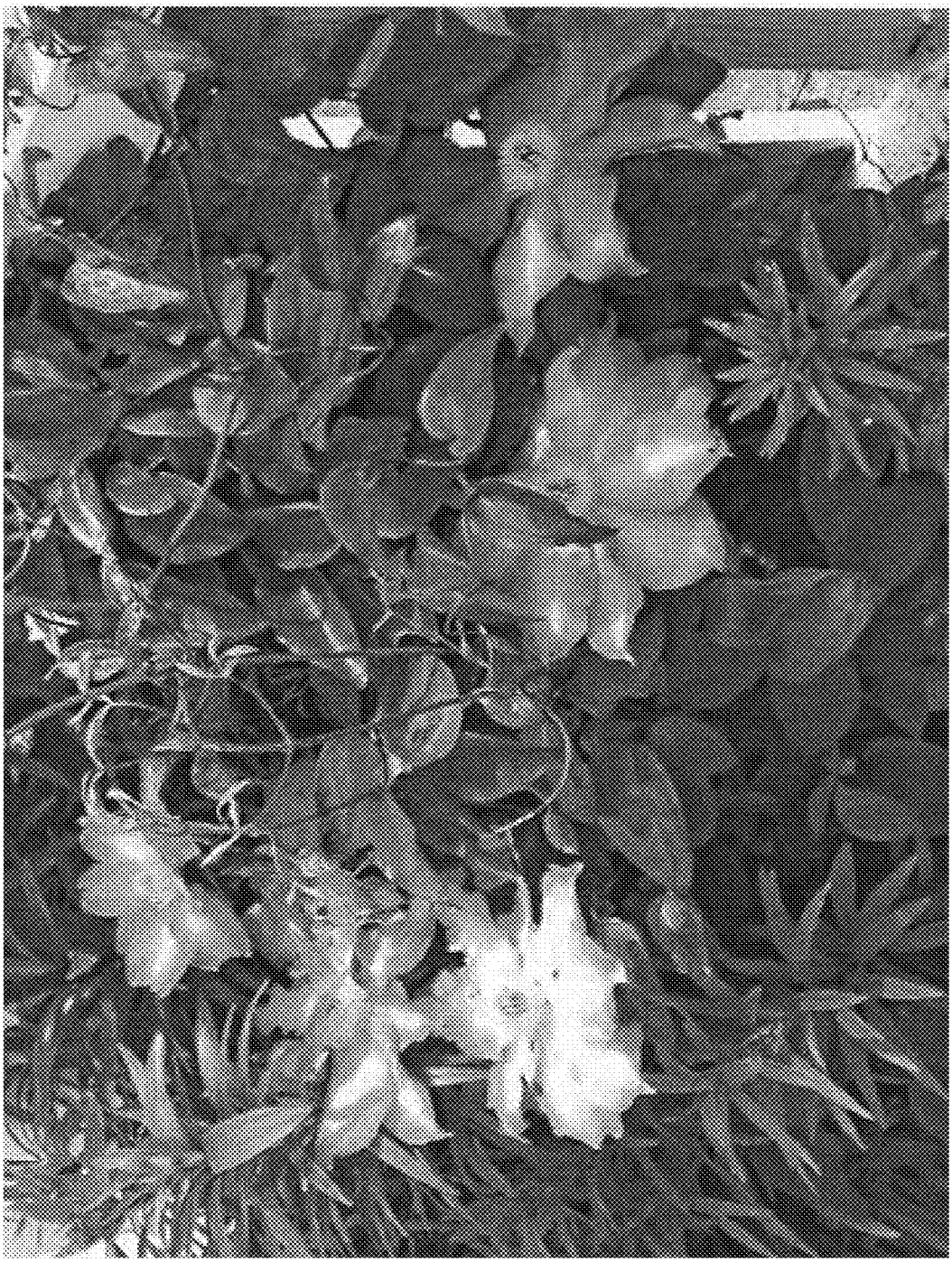

Latin name of the genus and species: *Clematis hybrida.*
Variety denomination: 'RobloM'.

BACKGROUND OF THE INVENTION

The new cultivar was found as a chance seedling among a group a mixed *Clematis* species and cultivars, in a commercial nursery in Christchurch, New Zealand. The inventors first discovered new variety in 1995. Due to the wide variety of species and cultivars grown at the nursery, the inventors are unable to distinguish the parentage.

Asexual reproduction of the new cultivar 'RobloM' by vegetative cuttings was first performed at the nursery in Christchurch, New Zealand during 1995, however, the cultivar was not commercially trialed or developed, and all progeny from the initial propagation were lost. In 2005, 'RobloM' was again propagated by vegetative cuttings and subsequently has shown that the unique features of this cultivar are stable and reproduced true to type on successive generations.

SUMMARY OF THE INVENTION

The cultivar 'RobloM' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'RobloM' These characteristics in combination distinguish 'RobloM' as a new and distinct *Clematis* cultivar:

1. Dark purple/pink sepals with a white bar.
2. Very early blooming.
3. Strong foliage.
4. Very rapid growth.

COMMERCIAL COMPARISON

Plants of the new *Clematis* can be compared to the commercial variety *Clematis* 'Violet Stargazer' unpatented. Plants of the new cultivar 'RobloM' are similar to plants of 'Violet Stargazer' in most horticultural characteristics, and are similar in having the unusual white bar pattern on the sepals, however, plants of the new cultivar have flowers that are more dark pink than violet blue. Additionally, the new cultivar blooms much earlier than 'Violet Stargazer.'

Plants of the new cultivar can also be compared to the commercial variety 'Bee's Jubilee' unpatented. 'RobloM' is similar to 'Bee's Jubilee' in most horticultural characteristics, including bloom time and growth habit, however, 'Bee's Jubilee' has sepals with a dark pink bar and pink background.

BRIEF DESCRIPTION OF THE PHOTOGRAPH

The accompanying photograph in FIG. 1 illustrates in full color a typical plant of 'RobloM' starting to flower in Spring, grown outdoors, in the ground in Christchurch New Zealand. Age of the plant photographed is approximately 2 years old, and was cut back to the ground the previous Fall. No additional lighting or chemical treatments were used. The photographs were taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Colour Chart except where general terms of ordinary dictionary significance are used. The following observations and measurements describe 'RobloM' plants grown outdoors in Christchurch, New Zealand. The growing temperature ranged from 20° C. to 35° C. during the day and approximately 10° C. to 18° C. at night. Age of the plant is approximately 2 years, and was cut back to the ground the previous Fall. No additional lighting or chemical treatments were used. Measurements and numerical values represent averages of typical plant types. No growth retardants were used.

Botanical classification: *Clematis hybrida* cultivar 'RobloM.'

PROPAGATION

Time to Initiate Roots: About 40 days at approximately 21° C.
Time to Produce a Rooted Cutting: About 60 days at 21° C.
Root Description: Typical Clematis root, fibrous and white-brown in color.

PLANT

Growth Habit: Vining, flowering plant. Evergreen to −5° C. Requires support to maintain upright habit. Typically, plants are pinched 2 to 3 times per year to encourage more branching.
Age of plant described: Approximately 2 years.
Container size: Described plant is in the ground, typically container size 15 cm.
Height: Approximately 1 meter per year, cut back to ground level in the Fall.
Plant spread: Approximately 2 meters per year.
Growth rate: Very rapid early in Spring, rapid after initial growth.
Branching Characteristics: Moderate branching occurs after pinch.
Length of Primary Lateral Branches: Approximately 80 to 100 cm.
Diameter of Lateral Branches: Aproximately 2.8 cm.
Internode length: Approximately 12 cm.
Stem texture: Very slight pubescence.
Stem Color: Near RHS Greyed-Red 180B.
Stem Strength: Moderate, flexible.

FOLIAGE

Leaf:
- *Arrangement.*—Simple.
- *Average length.*—Approximately 15 cm, including petiole, largest leaf section approximately 7 cm.
- *Average width.*—Approximately 4.5 cm.
- *Shape of blade.*—Elliptic.
- *Apex.*—Moderately Acute.
- *Base.*—Cordate.
- *Attachment.*—Petioled.
- *Margin.*—Entire.
- *Texture of top surface.*—Leathery.
- *Texture of bottom surface.*—Leathery.
- *Leaf internode length.*—Approximately 2.3 cm.
- *Color.*—Young foliage upper side: Near RHS Green 141C. Young foliage under side: Near RHS Yellow-Green 146B. Mature foliage upper side: Near RHS Green 141B. Mature foliage under side: Near RHS Green 138B.
- *Venation.*—Type: Pinnate. Venation color upper side: Near RHS Yellow-Green 144A. Venation color under side: Near RHS Yellow-Green 144A.
- *Petiole.*—Average Length: Approximately 8 cm. Color: Near RHS Greyed-Red 180B. Diameter: Approximately 0.1 cm. Texture: Smooth.

FLOWER

Natural flowering season: Naturally flower Spring through Summer.
Inflorescence type and habit: Single, axillary; flowers face mostly outward.
Rate of flower opening: Approximately 14 days from bud to fully opened flower.
Flower longevity on plant: 7 days, after fully opened. Self-cleaning.
Quantity of flowers: Free, continuous flowering, plants have at least 20 flowers at all times.
Inflorescence size:
- *Diameter.*—Approximately 16 cm.
- *Depth.*—Approximately 2 cm.

Corolla:
- *Tepal arrangement.*—Slightly overlapping, single whorl.
- *Quantity.*—Approximately 8.
- *Size.*—Length: 6 cm. Width: 3 cm.
- *Margin.*—Entire.
- *Apex.*—Acute.
- *Base.*—Truncate.
- *Texture.*—Smooth, velvety.

Color:
- *Tepals.*—When opening: Upper surface: Near RHS Red-Purple N74B with middle section streaked near RHS White N155B. Lower surface: Near RHS Red-Purple N74A.
- *Fully opened.*—Upper surface: Near RHS Red-Purple N74B with middle section heavily streaked near RHS White N155B. Lower surface: Near RHS Red-Purple N74B with middle section lightly streaked near RHS White N155B.
- *Ageing.*—Upper Surface: Near RHS Red-Purple N74C on edges, most of interior near RHS White N155B. Lower Surface: Near RHS N74C, mixed with White N155B.

Bud:
- *Shape.*—Ovate to Lanceolate.
- *Length.*—Approximately 5 cm.
- *Diameter.*—Approximately 2 cm.
- *Color.*—Near RHS N155B.

Pedicels:
- *Length.*—Approximately 6 cm.
- *Width.*—Approximately 0.2 cm.
- *Angle.*—Average 80°.
- *Strength.*—Moderate, flexible.
- *Color.*—Near RHS Yellow-Green 144C.

Fragrance: Slightly sweet.

REPRODUCTIVE ORGANS

Stamens:
- *Number.*—Approximately 100 per flower.
- *Anther length.*—0.8 cm.
- *Anther color.*—Near RHS Yellow 3B.
- *Anther shape.*—Oblong.
- *Pollen quantity.*—Profuse.
- *Pollen color.*—Near RHS Yellow 7A.
- *Filament length.*—Approximately 1.2 cm.
- *Filament aspect.*—Curved.
- *Filament color.*—Near RHS N155B.

Pistil:
- *Number.*—Approximately 100 per flower.
- *Length.*—Approximately 2.5 cm.
- *Shape.*—Spiraled.
- *Style color.*—Near RHS Greyed-White 156D.
- *Style length.*—Approximately 2 cm.
- *Stigma.*—Shape: spiraled. Color: Near RHS White 155D
- *Ovary color.*—Near RHS Greyed-Orange 165D. .

OTHER CHARACTERISTICS

Seeds and fruits: Not observed to date.

Disease/pest resistance: Neither resistance nor susceptibility to pathogens and pests common to *Clematis* have been observed.

Temperature tolerance: Tolerates temperatures from approximately −10 C. to 40° C.

What is claimed is:

1. A new and distinct cultivar of *Clematis* plant named 'RobloM' as herein illustrated and described.

* * * * *